United States Patent [19]

Grundei et al.

[11] Patent Number: 4,714,475
[45] Date of Patent: Dec. 22, 1987

[54] TIBIAL MEMBER OF A KNEE JOINT ENDOPROTHESIS

[75] Inventors: Hans Grundei, Lübeck; Reinhard Aigner, Munich, both of Fed. Rep. of Germany

[73] Assignee: S + G Implants GmbH, Lübeck, Fed. Rep. of Germany

[21] Appl. No.: 831,363

[22] Filed: Feb. 19, 1986

[30] Foreign Application Priority Data

Mar. 1, 1985 [DE] Fed. Rep. of Germany ....... 3507155

[51] Int. Cl.4 .............................................. A61F 2/38
[52] U.S. Cl. .................................................... 623/20
[58] Field of Search ................. 623/20, 19, 21, 22, 623/23

[56] References Cited

U.S. PATENT DOCUMENTS

| | | | |
|---|---|---|---|
| 2,719,522 | 10/1955 | Hudack | 623/23 |
| 3,886,601 | 6/1975 | Findlay | 623/20 |
| 4,355,427 | 10/1982 | Schneider | 623/19 |

FOREIGN PATENT DOCUMENTS 2039220 8/1980 United Kingdom ................. 623/20

Primary Examiner—Richard J. Apley
Assistant Examiner—David J. Isabella
Attorney, Agent, or Firm—Balogh, Osann, Kramer, Dvorak, Genova & Traub

[57] ABSTRACT

A tibia member of a knee joint endoprosthesis used as a replacement for a resectioned tibia head. The tibia member includes a bridge element having a shank anchored in the tibia and provided with a shackle or flap secured thereto at the front side thereof. An outer and concave pan member is provided at the lower extremity of the flap, the pan member having rounded-off edges for reception of tendon extremities. A convex clamping element is connected to the bridge element at the lower extremity of the flap for pressing the tendon extremities into the concave pan member, so that no sharp edges are thereby placed in contact with the tendon.

4 Claims, 2 Drawing Figures

TIBIAL MEMBER OF A KNEE JOINT ENDOPROTHESIS

BACKGROUND OF THE INVENTION

1. Field of the Invention

The invention relates to the tibial member of a knee joint endoprosthesis as a substitute for a resectioned tibia head, consisting of a shank which is to be anchored within the tibia and of a bridge element upwardly supporting the tibial endoprosthesis knee joint member, which is provided with a clamping element attachable by screw means, for the fastening of natural or artificial tendons.

2. Description of the Prior Art

In case of a resection of a tibia head, an endoprosthesis which has a shank anchored in the tibia is utilised as a substitute. The resection also severs the natural downwardly directed tendon of the patella, and the patella or the residual part of the natural tendon must thereupon be connected to one or two artificial tendons which should then be fastened to the bridging element of the tibia head endoprosthesis. This fastening operation was performed until now by means of clamps or collars, or windable securing wires or by retaining the natural or artificial tendon against a second plate by means of a clamping plate attachable by screw means, e.g. as apparent from DE-OS 24 00 834. To this end, the tendon was exposed to one or more acute deflections, so that it could be damaged at least after a particular period by being clamped tightly and could finally be severed. In this arrangement, the clamping plates were screwed to the patient's bones.

OBJECTS AND SUMMARY OF THE INVENTION

In the case of the implantation of the tibial member of a knee joint endoprosthesis, the object of the invention consists in being able to connect natural or artificial tendons to the tibial member of an endoprosthesis replacing the tibia head which is to be resectioned, in such manner that the tendons do not have to extend over sharp edges or holes, whereby they could incur damage and be finally caused to tear.

In the case of the initially referred to tibial member of a knee joint endoprosthesis, this problem is resolved in that the bridge element is provided with an outer and concave tray comprising rounded-off edges, for reception of a tendon extremity which may be pressed into the concave tray or pan by means of a convex clamping element. The procedure advantageously applied to this end is such that the convex pan is provided at the lower extremity of a shackle or flap firmly joined to the bridge element, and that this shackle merges into an outwardly projecting arcuate surface above the surface of the concave tray or pan.

Thanks to this solution according to the invention, the tendons which are to be clamped fast are firmly joined to the bridge element of the implant in a simple, reliable and durable manner without damaging actions. Thanks to this clamping method, it is also possible that one or both artificial tendons may first be passed through between the clamping element and the bridge element or the shackle joined to the bridge element, and to grasp the extremities for tensioning until the patella has reached its required position, and is correctly adjusted, whereupon the clamping element may be screwed on tightly and thereby unequivally grips fast the tendon or tendons.

BRIEF DESCRIPTION OF THE DRAWINGS

The invention is described in the following with reference to the drawings. In these.

DETAILED DESCRIPTION OF THE PREFERRED EMBODIMENT

Figures 1, 2:
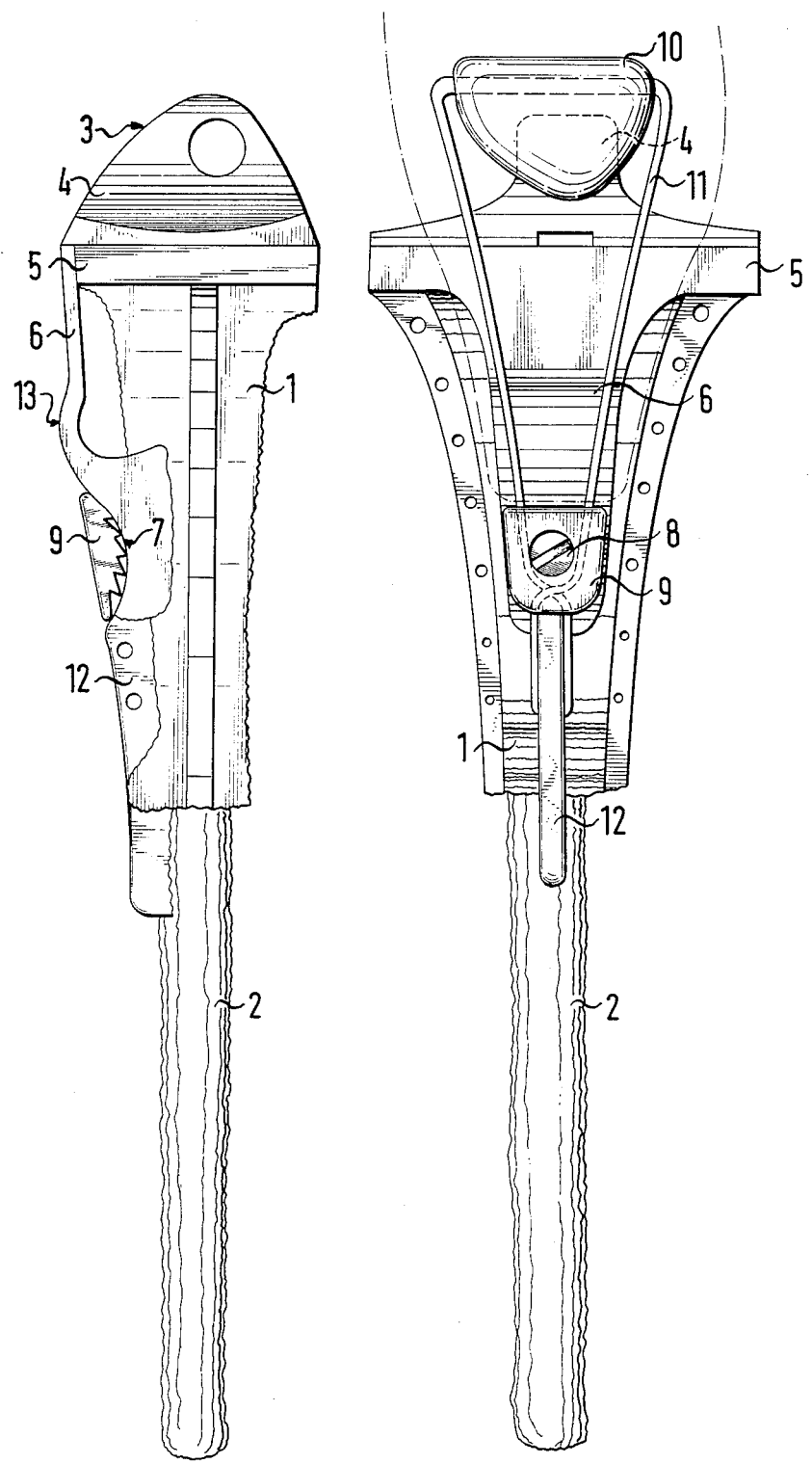
FIG. 1 shows a sideview of the tibial member of a knee joint endoprosthesis.
FIG. 2 shows a front view of the tibial member according to FIG. 1.

In a known manner, the replacement for a resectioned tibia head of a knee joint endoprosthesis comprises a metal bridge element 1 which is intended to have a shank 2 anchored in the tibia and is provided at the top with the joint member 3 whereof the friction surfaces situated at either side of a web 4 bear the ridges of the corresponding known femur joint member which is not illustrated.

In the region of its upper collar 5, the bridge element 1 is provided at the front side with a downwardly directed shackle or flap 6 which forms a clamping element together with a plate 9 which may be screwed on. The shackle or flap 6 is secured to the bridge element 1, at the upper and lower extremities threof, and is provided at the lower extremity with a concave and preferably partly cylindrical contact surface pan 7 matched by the convex rear side of the plate 9 which may be connected to the shackle 6 by means of a screw 8. The surface of the contact area 7 is advantageously finely roughened and the oppositely situated rear side of the plate 9 is contoured, e.g. with a saw-tooth shaped outline as indicated in FIG. 1.

For implanting the tibial prosthesis member, the patella marked 10 in FIG. 2, or the natural retaining tendon of the patella which is shown dash-dotted, is connected to a strap or tendon 11 of an appropriate plastics material, which is passed through downwards between the clamping plate 9 and the shackle 6 and is lodged behind the screw 8 in a crossed manner. The surgeon thus has the means by grasping and pulling on the extremities of the tendon 11 to set up the precise required position of the patella 10 and then of tightening the screw 8, whereby the tendon 11 is clamped fast between the plate 9 and the shackle 6. The clamping fast of the tendon 11 is concomitantly assisted by the contouring of the rear side of the plate and the roughened finish of the concave contact surface of the shackle. The downwardly directed free extremities of the tendon 11 are advantageously secured by being sewn for example, to a rib 12 provided with perforations below the shackle 6.

As apparent from FIG. 1, the tendons 11 led through between the pan 7 and the clamping element 9 do not run over sharp edges, and the shackle 6 is moreover provided in continuation of the concave pan 7 with an upwardly adjacent and outwardly projecting arc 13 which merges smoothly into the pan surface 7. This arc also has the advantage that the tendon cannot exert any excessive pressure on the joint members of the prosthesis during bending movements of the leg.

Whilst the invention and many of its attendant advantages will be understood from the foregoing description, it will be apparent that various changes may be made in the form, construction and arrangement of the parts without departing from the spirit and scope of the invention or sacrificing all of its material advantages,

What is claimed is:

1. In a tibial member of a knee joint prosthesis used as a substitute for a resectioned tibia head comprising a proximal joint portion connected to an intermediate bridge element, a distal stem portion extending distally from said bridge element adapted to be anchored in a prepared tibia and a clamping element adapted to be secured to said bridge element for fastening tendon extremities of a patella thereto, the improvement comprising said bridge element having front and rear surfaces wherein said front surface is provided with an elongated downwardly directed flap member secured thereto at a proximal region near said joint portion and at a distal region rear said stem; said flap member having formed in a distal region thereof a concave pan having rounded edges to cooperatively mate with a complementary convex rear surface of said clamping element whereupon engagement of said clamping element to said pan operatively secures said tendon extremities therebetween.

2. The improved tibia member according to claim 1, wherein the flap has an outwardly projecting arcuate surface above the area of said concave pan.

3. The improved tibia member according to claim 1 or 2, wherein the flap is provided at the lower extremity thereof and below said concave pan with a perforated rib for sewing on said tendon extremities.

4. The improved tibia member according to claim 1, wherein mutually confronted surfaces of said concave pan and of the convex clamping element are contoured or roughened.

* * * * *